US009180254B2

(12) United States Patent
Avery et al.

(10) Patent No.: US 9,180,254 B2
(45) Date of Patent: Nov. 10, 2015

(54) CODED FASTENER ASSEMBLY

(75) Inventors: Richard James Vincent Avery, Chipping Campdem (GB); Paul Draper, Evesham (GB); Aled Meredydd James, Dorridge (GB)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 313 days.

(21) Appl. No.: 13/642,076

(22) PCT Filed: Apr. 21, 2011

(86) PCT No.: PCT/EP2011/056481
§ 371 (c)(1),
(2), (4) Date: Dec. 21, 2012

(87) PCT Pub. No.: WO2011/131782
PCT Pub. Date: Oct. 27, 2011

(65) Prior Publication Data

US 2013/0090602 A1 Apr. 11, 2013

Related U.S. Application Data

(60) Provisional application No. 61/327,283, filed on Apr. 23, 2010.

(30) Foreign Application Priority Data

Jul. 29, 2010 (EP) .................................... 10171169

(51) Int. Cl.
*A61M 5/31* (2006.01)
*A61M 5/24* (2006.01)

(Continued)

(52) U.S. Cl.
CPC ............... *A61M 5/3129* (2013.01); *A61M 5/24* (2013.01); *A61J 1/062* (2013.01); *A61J 2205/40* (2013.01);

(Continued)

(58) Field of Classification Search
CPC ................ A61M 5/3129; A61M 5/24; A61M 2005/2488; A61M 2005/2407; A61M 2005/31588; A61M 2039/1094; A61M 2205/6045; A61J 2205/40; A61J 1/062
USPC ......................................... 604/189, 200, 232
See application file for complete search history.

(56) References Cited

U.S. PATENT DOCUMENTS 6,648,859 B2 * 11/2003 Bitdinger et al. ............. 604/232
2003/0004466 A1 1/2003 Bitdinger et al.
2003/0109834 A2 6/2003 Bitdinger et al.

FOREIGN PATENT DOCUMENTS

JP 2002-509469 3/2002
JP 2009-543629 12/2009

(Continued)

OTHER PUBLICATIONS

International Preliminary Report on Patentability for Int. App. No. PCT/EP2011/056481, mailed Nov. 1, 2012.

(Continued)

*Primary Examiner* — Theodore Stigell
*Assistant Examiner* — Amber Stiles
(74) *Attorney, Agent, or Firm* — McDonnell Boehnen Hulbert & Berghoff LLP

(57) ABSTRACT

Disclosed herein are fastening features for cartridge assemblies that include coding features that help dedicate a medicament reservoir to specific injection devices. An exemplary cartridge assembly comprises a cylindrical inner surface for holding medicament and a cylindrical outer surface comprising a fastening feature having a first coding element protruding from the cylindrical outer surface. The coding element is configured to engage a complementary coding feature on the fastener on a dose setting member specifically configured to dispense the medicament, thereby allowing only the correct cartridge assembly to connect to the correct dose setting member.

15 Claims, 14 Drawing Sheets

(51) Int. Cl.
*A61J 1/06* (2006.01)
*A61M 5/315* (2006.01)
*A61M 39/10* (2006.01)

(52) U.S. Cl.
CPC .................. *A61M 2005/2407* (2013.01); *A61M 2005/2488* (2013.01); *A61M 2005/31588* (2013.01); *A61M 2039/1094* (2013.01); *A61M 2205/6045* (2013.01)

(56) References Cited

FOREIGN PATENT DOCUMENTS

| | | | |
|---|---|---|---|
| WO | 99/16487 | 4/1999 | |
| WO | 2008/009645 | 1/2008 | |
| WO | 2008/059063 | 5/2008 | |
| WO | WO 2008059063 A1 * | 5/2008 | .............. A61M 5/24 |
| WO | 2008/074897 | 6/2008 | |
| WO | 2010/006870 | 1/2010 | |

OTHER PUBLICATIONS

International Search Report for Int. App. No. PCT/EP2011/056481, completed Oct. 13, 2011.

First Office Action for Chinese Patent Application No. 2011800310638, dated Mar. 25, 2014.

Japanese Office Action for Japanese Patent Application No. 2013-505496, dated Jan. 27, 2015.

Third Party Observations submitted for EP Application No. 11716249.5, dated Jun. 18, 2015.

* cited by examiner

CODED FASTENER ASSEMBLY

CROSS REFERENCE TO RELATED APPLICATIONS

The present application is a U.S. National Phase Application pursuant to 35 U.S.C. §371 of International Application No. PCT/EP2011/056481 filed Apr. 21, 2011, which claims priority to U.S. Provisional Patent Application No. 61/327,283 filed Apr. 23, 2010 and European Patent Application No. 10171169.5 filed Jul. 29, 2010. The entire disclosure contents of these applications are herewith incorporated by reference into the present application.

FIELD OF INVENTION

The present patent application is generally directed to the field of medical delivery devices. The devices may comprise a cartridge assembly and a dose setting member, in particular cartridge assemblies that have coded fastening assemblies for connection to dose setting members that have complementary fasteners with coding features to ensure the appropriate cartridge assembly is connected to the appropriate dose setting member.

BACKGROUND

Medicament reservoirs such as ampoules, cartridges, or vials are generally known. Such reservoirs are especially used for medicaments that may be self administered by a patient. For example, with respect to insulin, a patient suffering from diabetes may require a certain amount of insulin to either be injected via a pen type injection syringe or infused via a pump. With respect to certain known reusable pen type drug delivery devices, a patient loads a cartridge containing the insulin into a cartridge holder. The cartridge plus the holder is one type of cartridge assembly. After the cartridge has been correctly loaded, the user may then be called upon to select a dose of medicament. Multiple doses may be dosed from the cartridge. Once the cartridge is empty, the cartridge must be removed and replaced with a new cartridge. Most suppliers of such cartridges recommend that the user dispose of the empty cartridges properly.

Such known self-administration systems requiring the removal and reloading of empty cartridges have certain limitations. For example, in certain generally known systems, a user simply loads a new cartridge into the delivery system without the drug delivery device or without the cartridge having any mechanism of preventing cross use of an incorrect cartridge. That is, the drug delivery device does not have a mechanism for determining if the medicament contained in the cartridge is indeed the correct type of medicament to be administered by the patient. Alternatively, the drug delivery device does not present a mechanism for determining if the correct type of medicament within the cartridge should be used with that particular drug delivery system. This potential problem could be exacerbated given that certain elderly patients, such as those suffering from diabetes, may have limited manual dexterity. Identifying an incorrect medicament is quite important, since the administration of a potentially incorrect dose of a medicament such as a short acting insulin in lieu of a long insulin could result in injury or even death.

Some drug delivery devices or systems may use a color coding scheme to assist a user or care giver in selecting the correct cartridge to be used with a correct drug delivery device. However, such color coding schemes pose challenges to certain users, especially those users suffering from poor eyesight or color blindness: a situation that can be quite prevalent in patients suffering from diabetes.

Another concern that may arise with disposable replaceable cartridges is that these cartridges are manufactured in essentially standard sizes and must comply with certain recognized local and international standards. Consequently, such cartridges are typically supplied in standard sized cartridges (e.g., 3 ml cartridges). Therefore, there may be a variety of cartridges supplied by a number of different suppliers and containing different medicament but that may fit a single drug delivery device. As just one example, a first cartridge containing a first medicament from a first supplier may fit a medical delivery device provided by a second supplier. As such, a user might be able to load and then dispense an incorrect medicament (such as a rapid or basal type of insulin) into a drug delivery device without being aware that the medical delivery device was perhaps not designed or intended for use with such a cartridge and therefore the medicament contained within that cartridge.

As such, there is a growing desire from users, health care providers, care givers, regulatory entities, and medical device suppliers to reduce the potential risk of a user loading an incorrect drug type into a drug delivery device. There is also, therefore, a desire to reduce the risk of dispensing an incorrect medicament (or the wrong concentration of the medicament) from such a drug delivery device.

There is, therefore, a general need to physically dedicate or mechanically code the fastening features that allow cartridge assemblies, whether it is a cartridge holder or a molded cartridge without a separate holder, to be attached to dose setting portion of an injection device. In this way a particular drug type or types are linked to the appropriate injection device (e.g., dose setting member). Similarly, there is also a general need for a dedicated cartridge that allows the medical delivery device to be used with only an authorized cartridge containing a specific medicament and preventing undesired cartridge cross-use. There is also a general need to provide a dedicated fastening feature on the cartridge assembly that is difficult to tamper with so that the cartridge assembly may not be compromised in that the medicament can be used with an unauthorized drug or drug delivery device. Because such cartridge assemblies may be difficult to tamper with, they may also reduce the risk of counterfeiting: i.e., making it more difficult for counterfeiters to provide unregulated counterfeit products.

It is an object of the present disclosure to provide a novel element for a delivery device or a novel collection of elements for a delivery device, which facilitates provision of an improved delivery device. In particular, an element or a collection of elements should be provided which facilitates the provision of delivery devices with increased user safety.

This object may, for example, be achieved by the subject matter of the independent claim. Advantageous embodiments and refinements are subject matter of the dependent claims.

Apart from the subject matter covered in the claims, the description given herein also contains further advantageous aspects and features which may be combined with other features described herein even in connection with different aspects or embodiments to form other advantageous aspects or embodiments.

SUMMARY

This disclosure is generally directed to a fastening mechanism or assembly that has one or more integral coding features to ensure that a user of an injection device does not mistakenly use the incorrect medicament. In one aspect, a cartridge assembly, which may be defined as a cartridge in a holder or a, preferably molded, cartridge without a separate holder, for containing a reservoir of medicament is disclosed having a fastener at the proximal end (i.e. the end that attaches to a dose setting device or a dose setting member), which includes one or more coding features matched to a fastener located on the distal end of a dose setting device. The fastener/coding features operably connect the cartridge assembly to matched fastener/coding features on the dose setting device, thus allowing the user to administer an injection of the desired medicament.

The integral coding/fastener features can comprise combinations, such as, a pin and ridge, a pin and a pin, a ridge and a pair of pins, a pin and groove, and a screw thread. The use of detents to lock the cartridge assembly to the dose setting member is also advantageous. The cartridge assembly comprises a tubular member having a cylindrical inner surface and a cylindrical outer surface having a fastener comprising a first coding feature that is coded to engage a complementary coding feature on a complementary fastener on a dose setting member, thereby allowing the cartridge assembly to operably connect to the dose setting member. In alternative embodiments, the fasteners may be on an inner surface of the cartridge assembly, and on an outer surface of the dose setting member. The coding features integral with the cartridge assembly fastener and the complementary fastener on the dose setting assembly can be any combination of pins, ridges, ribs, grooves, slots, protrusions, valleys, and like structures provided that coding features are matched and allow to two assemblies to be operably connected, i.e. like a key in a lock or pieces in a jigsaw puzzle.

One aspect provides a collection comprising a plurality of cartridge assemblies each having one or more coded fasteners for connecting, in particular for operatively connecting, different medicaments, in particular reservoirs of different medicaments, to specifically matched dose setting members of the collection to make up a family of or a plurality of delivery devices, preferably injection devices. The medicaments may be operatively connected to the dose setting members to form a delivery device for administering or dispensing the medicament.

The collection comprises:

two or more cartridge assemblies, where a first cartridge assembly comprises, a) a first medicament; and b) a fastener.

The fastener comprises a first coding feature that is unique to the first medicament and is specifically coded to engage a complementary coding feature on a fastener on a first dose setting member that is configured to dispense the first medicament.

The first coding feature is different than a second coding feature on a fastener on a second cartridge assembly in the collection that contains a second medicament. The first and second medicaments are different. The second cartridge assembly is operably unconnectable, will not operatively connect and/or is prevented from being operatively connected to the first dose setting member, thereby preventing the first dose setting member from administering the second medicament.

In this way, using a medicament with the wrong dose setting member which may be designed to administer a different medication or medicament may be avoided and user safety may correspondingly be increased.

The fastener of the cartridge assembly may be operable to engage the fastener of the dose setting member to operatively connect the dose setting member and the cartridge assembly with one another. Preferably, after connection, a dose of the medicament contained in the cartridge assembly connected to the fastener may be set by operating one or more elements of the dose setting member and thereafter be dispensed from the device.

Preferably a unique coding feature is assigned to every medicament in the collection. Particular, the cartridge assembly or assemblies containing this particular medicament may be provided with a unique coding feature and the associated dose setting member for dispensing this medicament may be provided with a unique complementary coding feature.

The fasteners of the dose setting members and of the cartridge assemblies of the collection may be mechanically coded such that connection of a dose setting member and a cartridge assembly which have complementary fasteners is allowed, whereas connection of a dose setting member and a cartridge assembly which have non-complementary or incompatible fasteners is prevented.

The respective cartridge assembly may comprise a cartridge holder and/or or a cartridge. The respective cartridge holder may be configured to retain the associated cartridge within the cartridge holder. The respective cartridge assembly may comprise a tubular member. The respective medicament may be provided in the tubular member. The fastener of the respective cartridge assembly may be provided at a proximal end of the tubular member of that cartridge assembly. The tubular member of the respective cartridge assembly may have a cylindrical inner surface and a cylindrical outer surface. The fastener may be provided on the cylindrical inner surface or on the cylindrical outer surface, in particular at a proximal end or in a proximal end section.

The respective delivery device may comprise one of the dose setting members and one of the cartridge assemblies of the collection which are connected to each other to form the delivery device. The one or more fasteners of the dose setting member and the one or more fasteners of the cartridge assembly may have complementary coding features. The respective delivery device is preferably an injection device, like a pen-type injector, for example.

Another aspect provides a system or family of delivery devices, comprising a plurality of delivery devices, each delivery device comprising a cartridge assembly containing a medicament which is connected to an associated dose setting member to from the delivery device, the dose setting members and cartridge assemblies of the delivery devices are preferably chosen from a collection as described above. The cartridge assemblies and dose setting members are configured such that the cartridge assembly of one of the delivery devices is unconnectable, will not connect and/or is prevented from being connected to the dose setting member of another one of the delivery devices, e.g. an arbitrary one of the delivery devices which contains a different medicament, and/or such that the dose setting member of one of the delivery devices is unconnectable, will not connect and/or is prevented from being connected to the cartridge assembly of another one of the delivery devices, e.g. an arbitrary one of the delivery devices which contains a different medicament.

A further aspect provides a collection of cartridge assemblies having coded fasteners for connecting reservoirs of different medicaments to specific matched dose setting members making up a family of injection devices. Two or more cartridge assemblies make up a collection, where a first cartridge assembly comprises a tubular member having a cylindrical inner surface and a cylindrical outer surface, a first medicament inside the tubular member, and a fastener on the cylindrical outer or inner surface. The fastener comprises a first coding feature that is unique to the first medicament and is specifically coded to engage a complementary coding feature on a fastener on a first dose setting member that is configured to dispense the first medicament. The first coding feature is different than a second coding feature on a fastener that is located on a second cartridge assembly in the collection that contains a second medicament. This second medicament is different than the first medicament. Additionally, the second cartridge assembly will not operably connect to the first dose setting member thereby preventing the first dosing setting member from administering the second medicament.

In another embodiment the collection of cartridge assemblies can have a third cartridge assembly having a fastener comprising a third coding feature unique to a third medicament contained in the third cartridge assembly that is different than the first and second medicaments and where the third cartridge assembly operably connects only to a third dose setting member that is different from other dose setting members in the family of injection devices.

In another possible exemplary embodiment, the coding features may comprise at least one of (a) a ridge feature and (b) a pin feature, where the first coding is a ridge feature protruding from the cylindrical outer surface of the cartridge assembly and the complementary coding feature on the fastener of the dose setting member comprises a pin feature. This ridge and pin combination are unique to a specific medicament and are matched to allow the cartridge assembly and dose setting member to operably connect. Preferably, the ridge feature allows the cartridge holder to be connected to the dose setting member by movement of a first axial surface of the ridge feature in the axial direction along an axial surface of the pin feature, movement of a first helical surface of the ridge feature in the helical direction along a helical surface of the pin feature, and movement of a first rotational surface of the ridge feature in the rotational direction along a rotational surface of the pin feature. The cartridge assembly can only be connected to the device (i.e. dose setting member) if the two features (pin and ridge) of the fastener assembly match. In an alternative embodiment, the pin feature could be located on the cartridge assembly and the ridge feature located on the dose setting member. Likewise, the first coding feature protruding from the cylindrical outer surface could comprise a first pin feature, and the second coding feature on the dose setting member could comprise a second pin feature, thus forming a pin and pin combination.

In example embodiments of this disclosure the coding features may be achieved by varying the fastener or the fastener assembly or its features as follows:

(a) the number of coding features integral to the fastener assembly, preferably at least 1, but more preferably 2 or more;

(b) the position of the coding features, e.g. axial/circumferential/radial, especially relative to a standard feature, e.g. axial length from distal end. For example, a coding system for a collection of different medicaments may comprise fixed positions around the circumference where the coding features may be placed. For each medicament, coding features are placed only in some of these positions that are unique to each different medicament. Complementary or matching coding features that are integral to the fasteners on the dose setting members are configured to only dispense a specific medicament such that one dose setting member in the family or in the plurality of delivery devices cannot dispense a non-matching or wrong medicament;

(c) the size of the coding features, e.g. axial/radial/circumferential extent. The size of each feature may be different from at least one of the others, e.g., a number of pins with different radial extents; and/or (d) the cross-sectional shape of the coding features in any plane, e.g., transverse/longitudinal/radial/normal to the helix, or the cross-sectional shape of a stop feature.

This disclosure also includes coding systems for a range of different medicaments, where the coding feature integral to the fastener for each drug has a different shape. In order to ensure that a fastening feature, which the fastener may comprise, does not fit into the wrong mating part, preferably, the area covered by the fastening feature for one medicament must not be completely covered by the area of the fastening feature for any other medicament. In other words, each feature shape may be smaller in one area and larger in another than all of the other shapes, in particular than all of the other feature shapes, in the coding system. The shapes of the features may be complex, including indentations or protrusions along any of the edges of the shapes or features. Also the extent that each coding feature travels may be variable and may be any combination of directions:

(a) length for axial travel;

(b) pitch and/or angle turned for helical travel; and/or (c) angle turned for rotational travel.

The cartridge assembly may fit, in particular to the dose setting member, in one or more orientations. If the cartridge assembly fits in only one orientation, the number of coding combinations may be increased. This might be achieved if one or more coding features integral to the fastener (e.g., pins) has an asymmetric position or size around the axis, or if one of the features is unique, e.g., an indentation that is smaller than all the others. Coding may depend on the size or position in more than one dimension. A coding system for a collection of different medicaments may comprise or consist of a different fastening feature for each medicament, each of which may be smaller in one dimension and larger in another than all of the other features in the system. For example, a pin with a small circumferential extent will fit into the space for a wider pin, but if it has a larger axial extent it will not rotate. Alternatively, a pin with a small circumferential extent may have a large radial extent, and therefore the cartridge assembly cannot be inserted into the wrong device. Each feature may be offset in an axial direction relative to the others, increasing the number of coding combinations, and in addition, the fastening features may have an asymmetric position or size relative to each other when viewed along a longitudinal axis. In some embodiments all pins are on the dose setting member, the pins could equally be on the cartridge assembly or alternatively, one or more pins could be on the cartridge assembly, and the rest on the dose setting member.

Coding may block all incorrect drugs or just the most dangerous, e.g. a short-acting drug can be fitted into a device intended for long-acting drugs, or a low concentration drug into a device for high concentration, but not vice versa. Chamfers or ramped/helical surfaces may help the user to align coding on the cartridge assembly with coding on the device. Coding features may be detected by electro-mechanical means, e.g. micro-switches, or optical/magnetic switches. A programmable pen could then respond to the drug type, e.g. by limiting the maximum dose.

Coding may include the use of detents where the fastener is coded by its position relative to a detent that locks the cartridge assembly into place. If a cartridge assembly is connected to an incompatible device, either it would not be locked into place, or its travel would be blocked. A spring may force an incorrect cartridge assembly out of the device. In one possible embodiment, different user actions distinguish between different drugs, such that they either prevent the fastening of the device, or highlight to the user that the components are not compatible. For example, reversing the hand of a bayonet or other type of fastener assembly. The following are possible options or modifications:

(a) similar fastener assembly, but opposite in direction i.e. clockwise or anticlockwise engagement;

(b) similar fastener assembly, but with longer or shorter travel to engage the fastening features; and/or (c) substantially different fastening methods to distinguish between drugs, for example, rotational fit (e.g. bayonet or screw thread) versus an axial fit (e.g. snap-fit).

In another embodiment, a first coding feature which may protrude from the cartridge assembly, preferably from an outer surface thereof such as from a cylindrical outer surface, may comprise a pair of pins, and the matching or complementary coding feature on the dose setting member may comprise a ridge feature. The pin features may be axially offset from each other. In this embodiment, to connect the cartridge holder to the dose setting member, the first pin feature may engage a distal edge of the ridge feature and the second pin feature may engage a proximal edge of the ridge feature. In a further aspect, the dose setting member includes a second ridge feature, which may be symmetrical, in particular across a diameter of the outer cylindrical wall or the cylindrical outer surface, to the first ridge feature. The first and second ridge features (possibly in conjunction with one or more additional coding features), may form gates at a proximal end of the dose setting member fastener. The gates may operate to accept pin features on correct cartridge assemblies and either provide an indication that a dose setting member does not match the cartridge holder, or prevent mismatched dose setting members and cartridge holders from being connected. The pins on the cartridge assembly may be oblong in shape in the circumferential extent. In some cases it may be advantageous to have the pins on the dose setting member and the ridges on the cartridge assembly.

Alternatively, the cartridge assembly could be fastened to the dose setting member by a pin that is guided along a groove, where the pin could be located on the cartridge holder and the groove on the dose setting member or vice versa. In such a fastener or fastener assembly the pin and groove may be configured to match and therefore prevent attaching the wrong cartridge assembly to the wrong dose setting member.

Yet another alternative is where the coding feature integral to the fastener is a screw thread and a different thread type could be used for (or matched to) each different medicament in a collection of cartridge assemblies. In the case of a thread, the coding feature could be the crest of the thread with each having a different circumferential extent to the trough, or turns in the thread would be unequally spaced around the circumference. In another example, a thread with a small circumferential extent will fit into the space for a wider thread, but if it has a larger axial extent it will not rotate. Alternatively, a thread with a small circumferential extent may have a large radial extent, and therefore the cartridge assembly cannot be inserted into the device.

In the following text, a set of particularly advantageous aspects of this disclosure is described. The aspects are denoted by numbers, which facilitates referencing the features contained in specific aspects by the respective number. These aspects are:

1. A collection of cartridge assemblies each having coded fasteners for connecting reservoirs of different medicaments to specific matched dose setting members to make up a family of injection devices comprising:

two or more cartridge assemblies, where a first cartridge assembly comprises, a) a tubular member having a cylindrical inner surface and a cylindrical outer surface;

b) a first medicament inside the tubular member; and c) a fastener on the cylindrical outer or inner surface at a proximal end comprising a first coding feature that is unique to the first medicament and is specifically coded to engage only a complementary coding feature on a fastener on a first dose setting member that is configured to dispense the first medicament, wherein the first coding feature is different than a second coding feature on a fastener on a second cartridge assembly in the collection that contains a second medicament, where the first and second medicaments are different and where the second cartridge assembly will not operably connect to the first dose setting member, thereby preventing the first dosing setting member from administering the second medicament.

2. The collection of aspect 1, further comprising a third cartridge assembly having a fastener comprising a third coding feature unique to a third medicament contained in the third cartridge assembly that is different than the first and second medicaments and where the third cartridge assembly operably connects only to a third dose setting member that is different from other dose setting members in the family of injection devices.

3. The collection of aspect 1, wherein all the fasteners of the cartridge assemblies in the collection are of the same type selected from the group consisting of threads, pins & grooves, pins & ridges, bayonet, snap-fit, and detents, and wherein each coding feature on each fastener is different from all the other coding features on the other fasteners on the cartridge assemblies in the collection.

4. The collection of aspect 1, wherein each fastener on each of the cartridge assemblies in the collection are a different type and are selected from the group consisting of threads, pins & grooves, pins & ridges, bayonet, snap-fit, and detents, and wherein each coding feature on each fastener is different from all the other coding features on the other fasteners on the cartridge assemblies in the collection.

5. The collection of aspect 1, where each fastener in the collection of cartridge assemblies has two or more coding features.

6. The collection of aspect 1, where each coding feature of each fastener in the collection of cartridge assemblies comprises at least one protrusion that has a ridge feature and where all the complementary coding features on all of the dose setting members in the collection comprise a pin feature configured to engage the ridge feature.

7. The collection of aspect 1, where each coding feature of each fastener in the collection of cartridge assemblies comprises at least one groove configured to accept a pin located on all the complementary coding features on all of the dose setting members in the collection.

8. The collection of aspect 1, where each fastener in the collection of cartridge assemblies comprises a screw thread and each coding feature of each fastener has a different pitch, number of turns, or angle of threads that is unique to a specific medicament.

9. The collection of aspect 1, where each coding feature of each fastener in the collection of cartridge assemblies comprises at least one pin and where all the complementary coding features on all of the dose setting members in the collection comprise a complementary pin feature.

These as well as other advantages of various aspects of the present disclosure will become apparent to those of ordinary skill in the art by reading the following detailed description, with appropriate reference to the accompanying drawings.

BRIEF DESCRIPTION OF THE DRAWINGS

Exemplary embodiments are described herein with reference to the drawings, in which:

FIG. 11A shows coded by its circumferential extent and axial position and FIG. 11B shows a pin with a small circumferential extent and a large radial extent;

DETAILED DESCRIPTION

Figure 1:
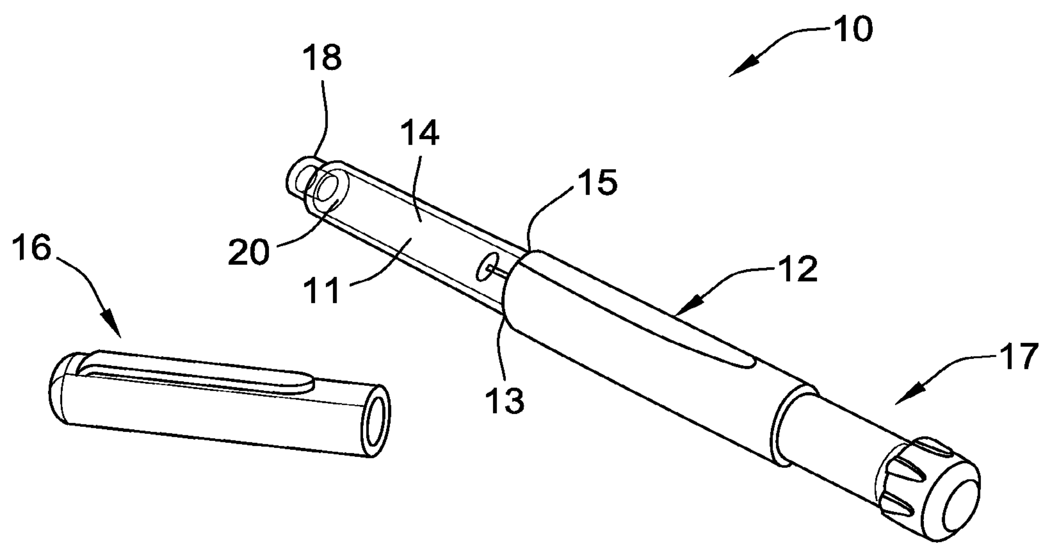
FIG. 1 illustrates a pen type drug delivery device.

Referring to FIG. 1, there is shown a drug delivery device 10 in the form of a pen type device, in particular a pen type syringe. This drug delivery device 10 comprises a dose setting member 12, a cartridge holder 14, and a removable cap 16. A proximal end 15 of the cartridge holder 14 and a distal end 13 of the dose setting member 12 are removably or releasably secured together. The pen type syringe may comprise a re-usable or a disposable pen type device or syringe. Where the syringe comprises a re-usable device, the cartridge holder 14 and the dose setting mechanism are removably or releasably coupled together. In a disposable device, they are permanently coupled together. When the drug delivery device is not in use, a removable cap 16 can be releasably retained over the cartridge holder 14.

Figure 2:
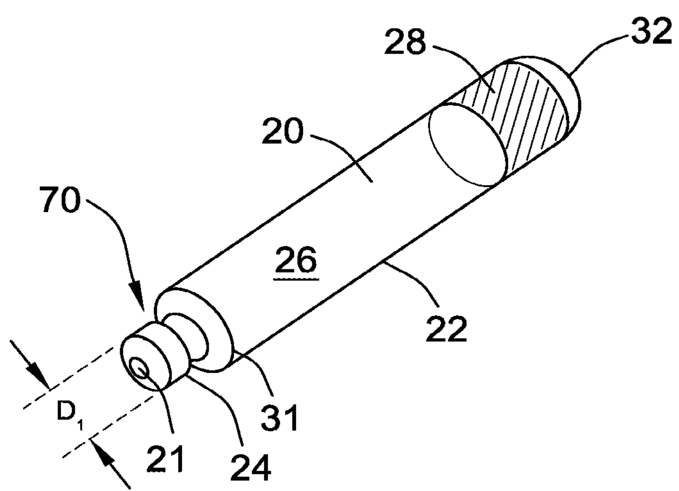
FIG. 2 illustrates a cartridge that may be loaded into a cartridge holder of the pen type drug delivery device illustrated in FIG. 1.

The cartridge holder contains a, preferably removable, cartridge 20 containing a medicament 26. Referring to FIG. 1, the cartridge holder 14 houses a removable cartridge 20. FIG. 2 illustrates a perspective view of the cartridge 20 that may be used with the drug delivery device illustrated in FIG. 1.

An inner cartridge cavity 11 defined by the cartridge holder 14 is dimensioned and configured to securely receive and retain the cartridge 20. The cartridge 20 includes a generally tubular barrel 22 extending from a distal end 70 to a proximal end 32. A pierceable seal or septum 21 is securely mounted across the open distal end 70 defined by a neck. The seal 21 may be held in place by a metallic sleeve 24. This sleeve 24 may be crimped around the circumferential bead at the distal end of the neck. The medicament 26 is pre-filled into the cartridge 20 and is retained within the cartridge, in part, by the pierceable seal 21, the metallic sleeve 24, and the stopper or piston 28. The movable stopper or piston 28 is retained in a first end or proximal end of the cartridge 20. The stopper 28 is in sliding fluid-tight engagement with the inner tubular wall of the barrel 22. Forces directed axially in the distal direction upon the stopper 28 during dose administration urges the medication 26 from the cartridge though a double ended needle mounted onto the distal end of the cartridge holder 14.

A number of doses of a medicament 26 may be dispensed from the cartridge 20. Preferably, the cartridge 20 contains a type of medicament 26 that must be administered often, such as once or more times a day. One such medicament is insulin.

For the purposes of this disclosure the collection of cartridge assemblies each may contain a number of different medicaments. This means the collection can contain the same active ingredient, such as insulin, but with each cartridge assembly containing a different concentration or type of insulin or both. Likewise, some of the cartridge assemblies can contain different active ingredients, for example, some containing insulin and some containing GLP-1. In any event, as used here the term "insulin" shall mean Insulin, insulin analogs, insulin derivatives or mixtures thereof, including human insulin or a human insulin analogs or derivatives. Examples of insulin analogs are, without limitation, Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin or Des(B30) human insulin. Examples of insulin derivatives are, without limitation, B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(w-carboxyheptadecanoyl)-des(B30) human insulin and B29-N-(ω-carboxyheptadecanoyl) human insulin.

As used herein the term "GLP-1" shall mean GLP-1, GLP-1 analogs, or mixtures thereof, including without limitation, exenatide (Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-$NH_2$), Exendin-3, Liraglutide, or AVE0010 (H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Ser-Lys-Lys-Lys-Lys-Lys-Lys-$NH_2$). GLP-1 is a glucagon-like peptide-1, which is derived from the transcription product of the proglucagon gene and is found in the body where it is secreted by the intestinal L cell as a gut hormone. GLP-1 possesses several physiological properties that make it (and its analogs) a subject of intensive investigation as a potential treatment of diabetes mellitus.

Examples of beta agonists are, without limitation, salbutamol, levosalbutamol, terbutaline, pirbuterol, procaterol, metaproterenol, fenoterol, bitolterol mesylate, salmeterol, formoterol, bambuterol, clenbuterol, indacaterol.

Hormones are for example hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A portion of the cartridge holder 14 defining the cartridge holder cavity 11, which is formed by the inner cylindrical wall of cartridge holder 14, is of substantially uniform diameter and is greater than the cartridge diameter of cartridge 20 represented in FIG. 2 by $D_1$. The cartridge holder cavity may have a tubular shape as may the cartridge, at least in a section. The interior of the cartridge holder includes an inwardly-extending annular portion or stop 18 that is dimensioned to prevent the cartridge 20 from moving within the cartridge holder 14. In this manner, when the cartridge 20 is loaded into the cavity 11 of the cartridge holder 14 and the cartridge holder 14 is then connected to the dose setting member 12, the cartridge 20 will be securely held within the cartridge cavity.

The dose setting member 12 comprises a dose setter 17 at the proximal end of the dose setting member. The dose setter 17 may be moved with respect to a body of the dose setting member 12 to set a dose. In one preferred arrangement, the dose setter 17 is rotated to set a dose. To administer this set dose, the user attaches the needle assembly (not explicitly shown) comprising a double ended needle on the distal end of the cartridge holder. In this manner, the needle assembly pierces the seal 21 of the cartridge 20 and is therefore in liquid communication with the medicament 26. The user pushes on the dose setter 17 to inject the set dose. The same dose setting and dose administration procedure is followed until the medicament 26 in the cartridge is expended and then a new cartridge must be loaded in the device. To exchange an empty cartridge, the user is called upon to remove the cartridge holder 14 from the dose setting member 12.

Figure 3A:
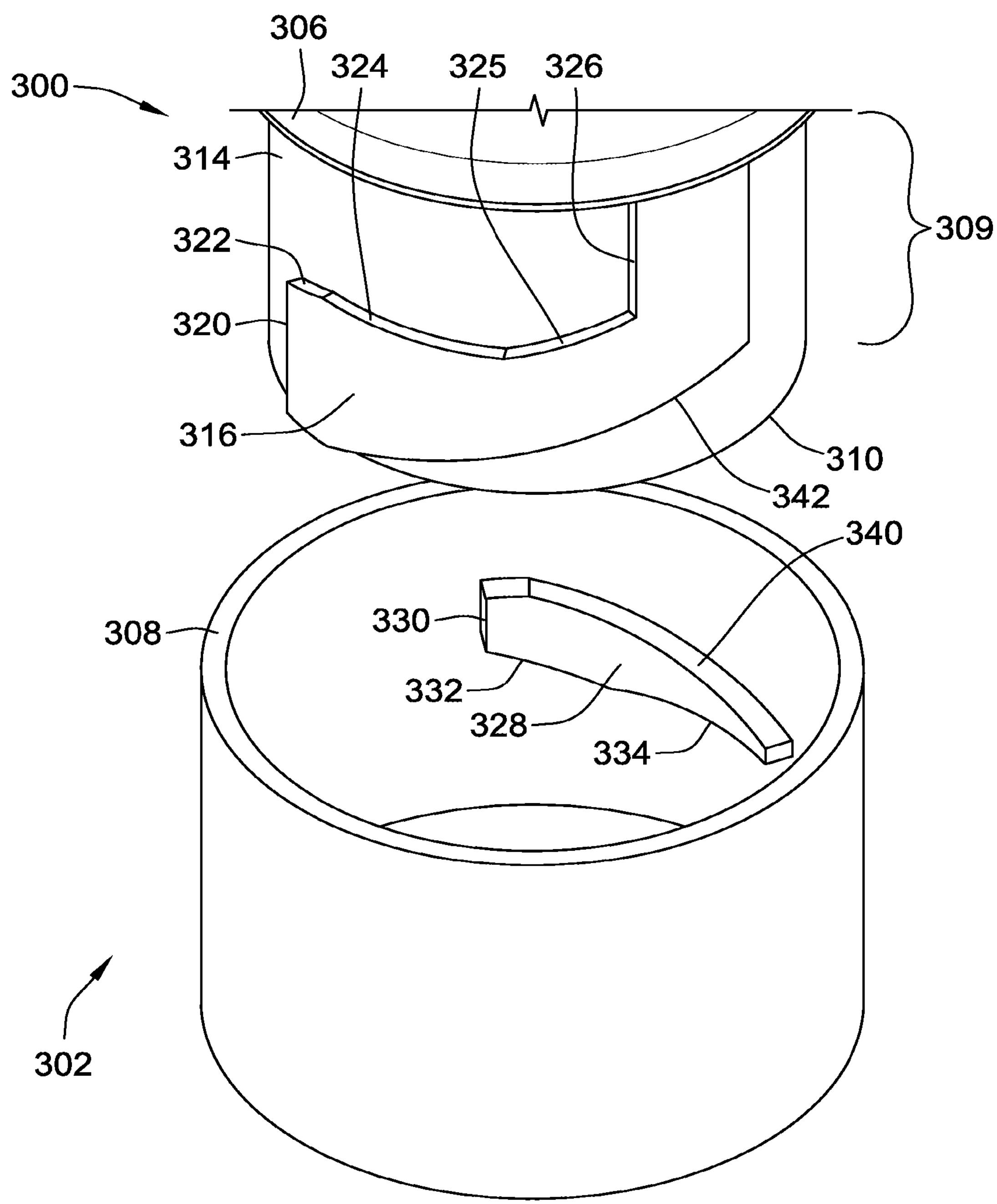
FIG. 3A illustrates an arrangement of a cartridge assembly that includes coding features that help dedicate the cartridge assembly to a particular dose setting member.

FIG. 3A illustrates one arrangement of this disclosure where a cartridge holder 300 that includes a fastener having coding features that help dedicate the cartridge holder 300 to a particular dose setting member 302. The cartridge holder or assembly 300 has a tubular body having a cylindrical inner surface that defines the cavity designed to hold a medicament cartridge. Such a medicament cartridge could comprise a glass cartridge or alternatively a molded cartridge made from a plastic such as a COC, COP, PBT, LDPE, or HDPE type plastic that may incorporate a ridge connector, and therefore eliminate the need for a separate cartridge holder. The tubular body extends from the stop (not shown) to a shoulder 306. Shoulder 306 is arranged such that when cartridge holder 300 is connected to dose setting member 302, the proximal side of shoulder 306 sits flush against the distal end 308 of the dose setting member 302.

A connector or fastener portion 309 of cartridge holder 300 extends from the shoulder 306 to a proximal end 310 of cartridge holder 300 and includes one or more coding or ridge features 316. Connector portion 309 defines a cylindrical inner wall and a cylindrical outer wall 314, and ridge feature 316 protrudes radially from the cylindrical outer wall 314.

The ridge feature 316 may take on a variety shapes and is generally defined by a raised or protruded area in between a distal edge and a proximal edge, extending axially from shoulder 306 to proximal end 310. In general, a "ridge feature" may be any protrusion that covers a portion of an area extending from shoulder 306 to proximal end 310. The distal edge of ridge feature 316 includes a first axial surface 320, a first helical surface 322, a rotational surface 324, a second helical surface 325, and a second axial surface 326, which together extend from shoulder 306 to proximal end 310. This embodiment is not limited to the precise shapes of the surfaces illustrated in FIG. 3A and any configuration of axial surface, rotational surface, followed by an axial surfaces may be used.

The dose setting member 302 includes a matched fastener/coding arrangement with a pin feature 328 protruding from an inner cylindrical wall of the dose setting member 302. The pin feature 328 and the ridge feature 316 may protrude substantially the same radial distance D (i.e., have the same radial extent) inward from the dose setting member 302 and outward from the cartridge holder 300, respectively. Alternatively, ridge feature 316 and pin feature 328 may have different radial extents. The cylindrical outer wall 314 of cartridge holder 300 has a radius $R_1$, and the inner cylindrical wall of dose setting member 302 has a radius $R_2$. When the connector portion 309 is inserted into dose setting member 302, $R_2$ and $R_1$ generally define a cylindrical gap between connector portion 309 and the inner cylindrical wall of dose setting member 302. In one embodiment, the cylindrical gap is typically of a radial extent substantially equal to or just slightly different from D, such that ridge feature 316 and pin feature 328 substantially fill the width of the gap and thus secure the cartridge holder 300 when connector portion 309 is inserted into dose setting member 302.

To help provide cartridge dedication, the ridge feature 316 of cartridge holder 300 is preferably coded to match the pin feature 328 of dose setting member 302. In general, a "pin feature" may be any protrusion that leaves an axial gap between the pin feature 328 and the proximal end (end opposite 308) of the internal cylindrical housing of dose setting member 302. As shown, pin feature 328 includes an axial surface 330, a helical surface 332, and a rotational surface 334. As such, the cartridge holder 300 may be securely connected to the dose setting member 302 by inserting the connector portion 309 into the dose setting member 302, and guiding the axial, rotational, and helical surfaces of pin feature 328 along the appropriate surfaces of ridge feature 316.

Figure 3B:
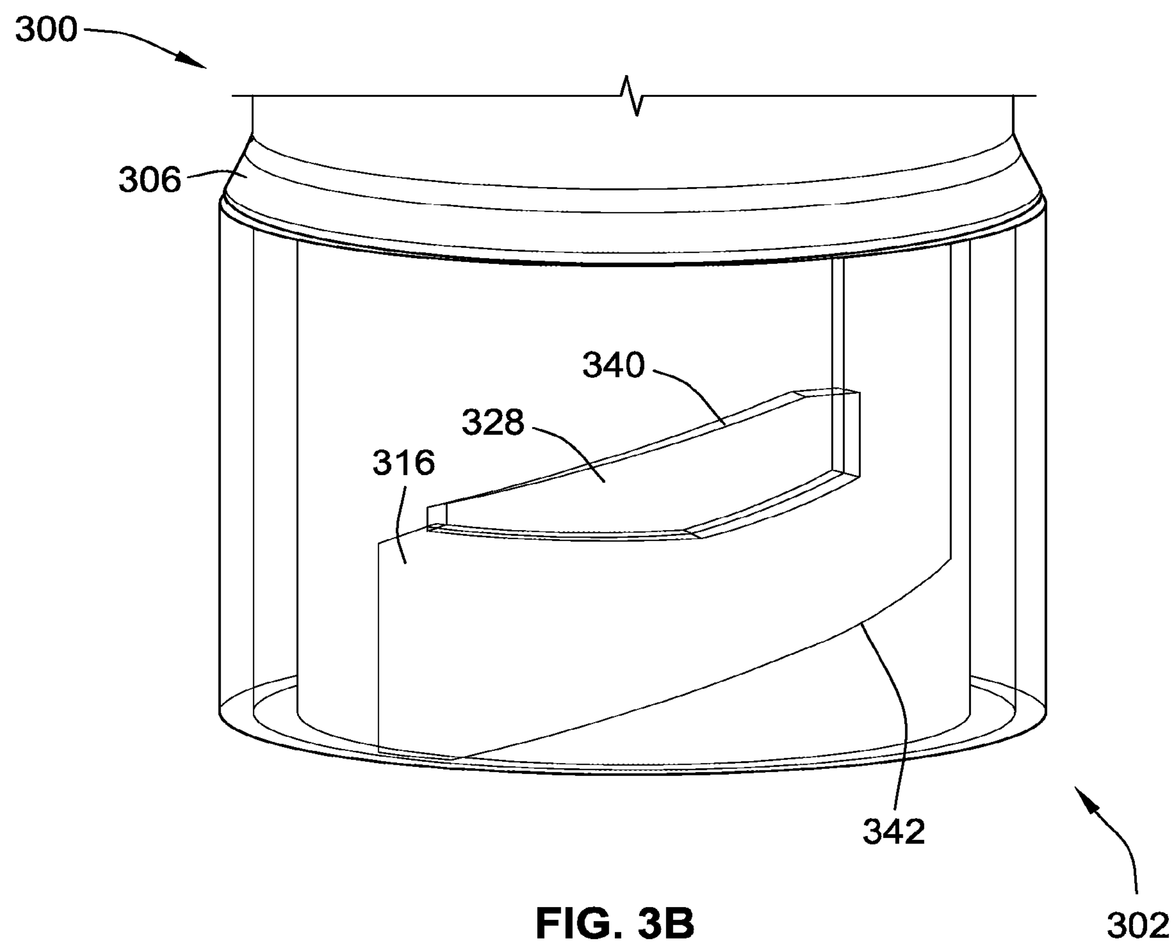
FIG. 3B illustrates another arrangement of a cartridge assembly that includes coding features that help dedicate the cartridge assembly to a particular dose setting member.

More specifically, cartridge holder 300 may be secured to the dose setting member 302, by performing the following: (1) contacting the first axial surface 320 of the ridge feature 316 to the axial surface 330 of the pin feature 328 and moving the first axial surface 320 of the ridge feature 316 along the axial surface 330 of the pin feature 328; (2) moving the first helical surface 322 of ridge feature 316 along the helical surface 332 of the pin feature 328; and (3) moving the rotational surface 324 of ridge feature 316 along the rotational surface 334 of the pin feature 328 until the second helical surface 325 and the second axial surface 326 of the ridge feature 316 contact the helical surface 332 and the axial surface 330 of pin feature 328, respectively, thereby preventing further movement in the rotational and helical directions. Preferably, when connected as such, the shoulder 306 also contacts the distal end 308 of dose setting member 302, and combined with the contacting of the ridge feature 316 to the pin feature 328, prevents further movement in an axial direction. More generally, in a preferred embodiment, connecting the cartridge holder 300 to the dose setting member 302 involves movement of the cartridge holder (guided by the movement of the ridge feature 316 along the pin feature 328), first in the axial direction and then in a rotational direction. FIG. 3B shows the relative positions of the ridge feature 316 and pin feature 328 when properly connected as described above. When connected as such, the ridge feature 316 and pin feature 328 help securely connect the cartridge holder 300 to the dose setting member 302. If the ridge feature and pin feature do not match correctly, the connection will not be secure, which indicates to a user that they are not using the correct cartridge holder and/or dose setting member.

Figure 3C:
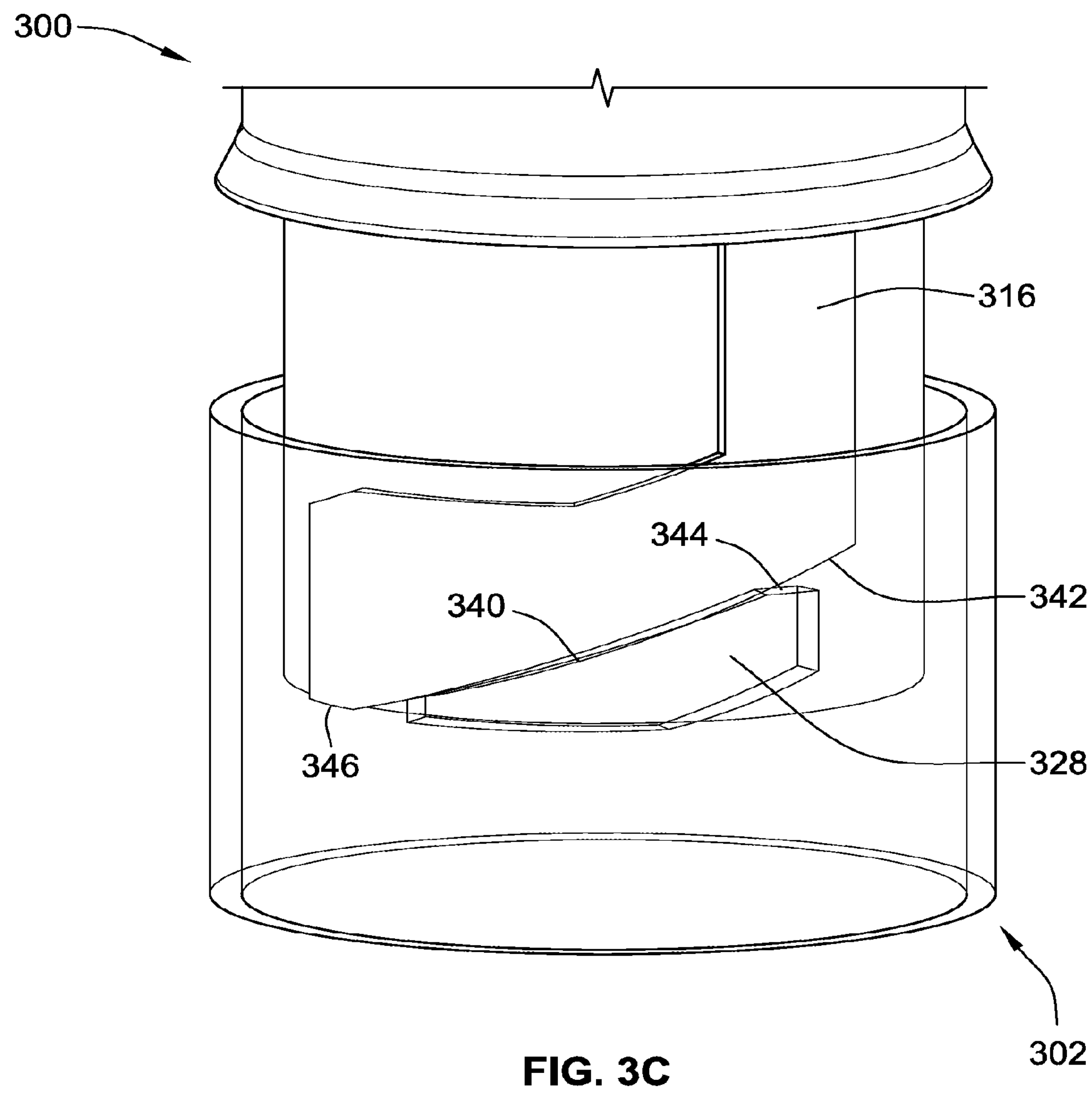
FIG. 3C illustrates another arrangement of a cartridge assembly that includes coding features that help dedicate the cartridge assembly to a particular dose setting member.

In a further aspect, illustrated in FIG. 3C, pin feature 328 may include a helical surface 340 that helps the user with initial alignment of the cartridge holder 300 and/or dose setting member 302, so that the cartridge holder 300 and dose setting member 302 can be connected as described above. Specifically, the user can insert the cartridge holder 300 axially into the dose setting member, so that the helical surface 340 of pin feature 328 contacts helical surface 342 of the ridge feature. This contact causes the cartridge holder to rotate in a clockwise direction relative to the dose setting mechanism, until the ridge reaches the end of the pin, when the ridge and pin are correctly aligned for connection as described above.

Returning to FIG. 3A, it should be understood that alternatively, the ridge feature 316 and/or the pin feature 328 may be arranged such that the order in which the cartridge holder 300 is moved in the axial direction, the rotational or helical direction, and/or the radial direction may vary. In addition, the length of the various surfaces of the ridge feature and/or pin feature may vary, thereby coding different ridge features to match different pin features, and vice versa. As such, the amount of movement in a given direction or directions (e.g., movement in the axial, helical, and/or radial directions) involved in connecting cartridge holder 300 to the dose setting member 302 may vary in proportion to the length of the various surfaces. Further, it should be understood that the arrangement of surfaces making up ridge feature 316 may vary, and that the ridge feature may include a single axial surface or multiple axial surfaces, a single helical surface or multiple helical surfaces, and/or a single rotational surface or multiple rotational surfaces.

Other variations on the embodiment illustrated in FIG. 3A are also possible. For example, the connector portion 309 of the cartridge holder 300 may include one ridge feature (as shown) or multiple ridge features, which may be the same or different in structure. Similarly, the dose setting member 302 may include one pin feature (as shown) or multiple pin features, which may be the same or different in structure. Moreover, it is possible to have the coding features vary in more than one dimension, e.g. varying the axial/radial/circumferential extent. The size of each feature may be different from at least one of the others.

Figure 4A:
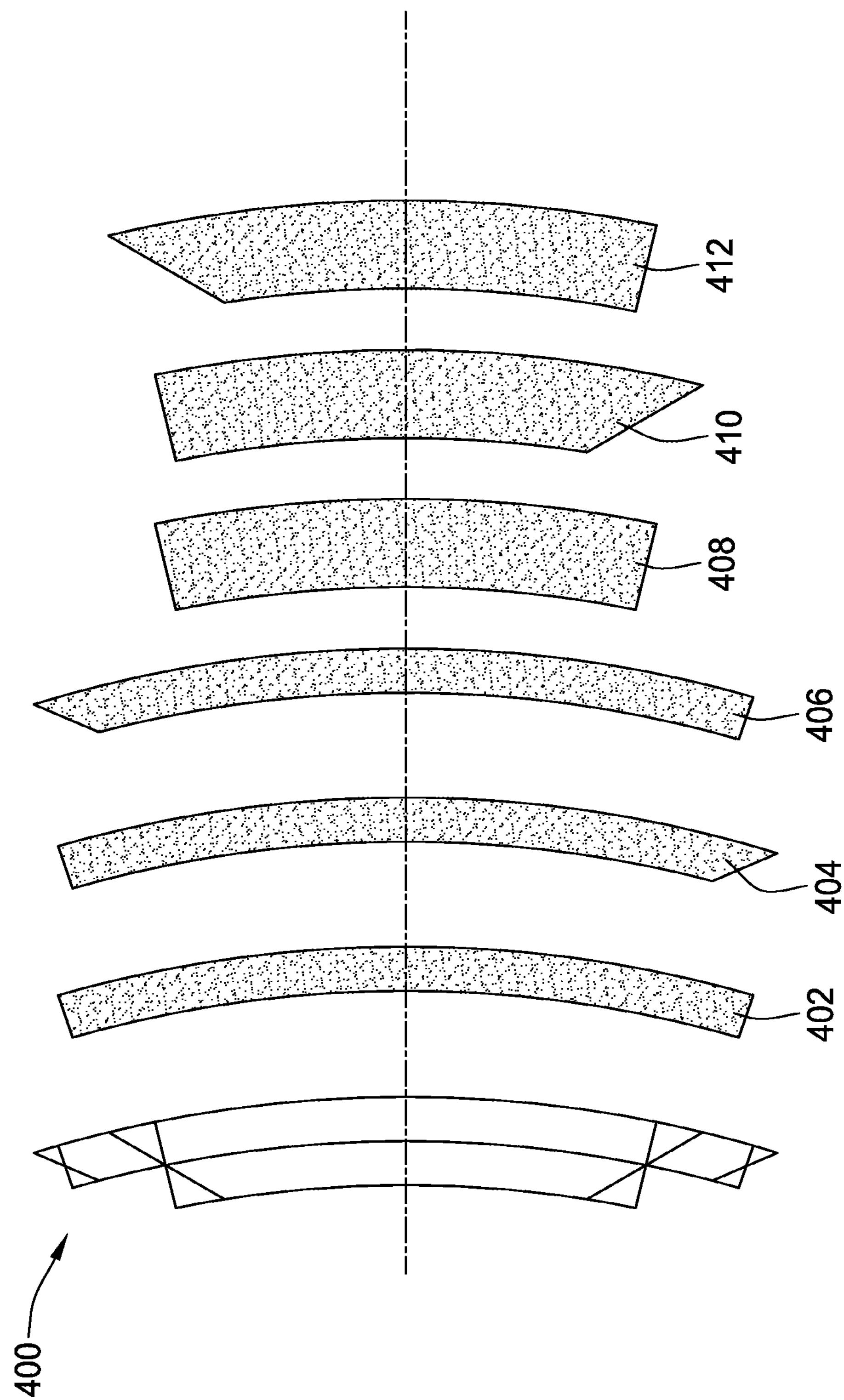
FIG. 4A shows cross-sections of different fastening features that may be used for different drugs, drawn on a transverse plane.
Figure 4B:
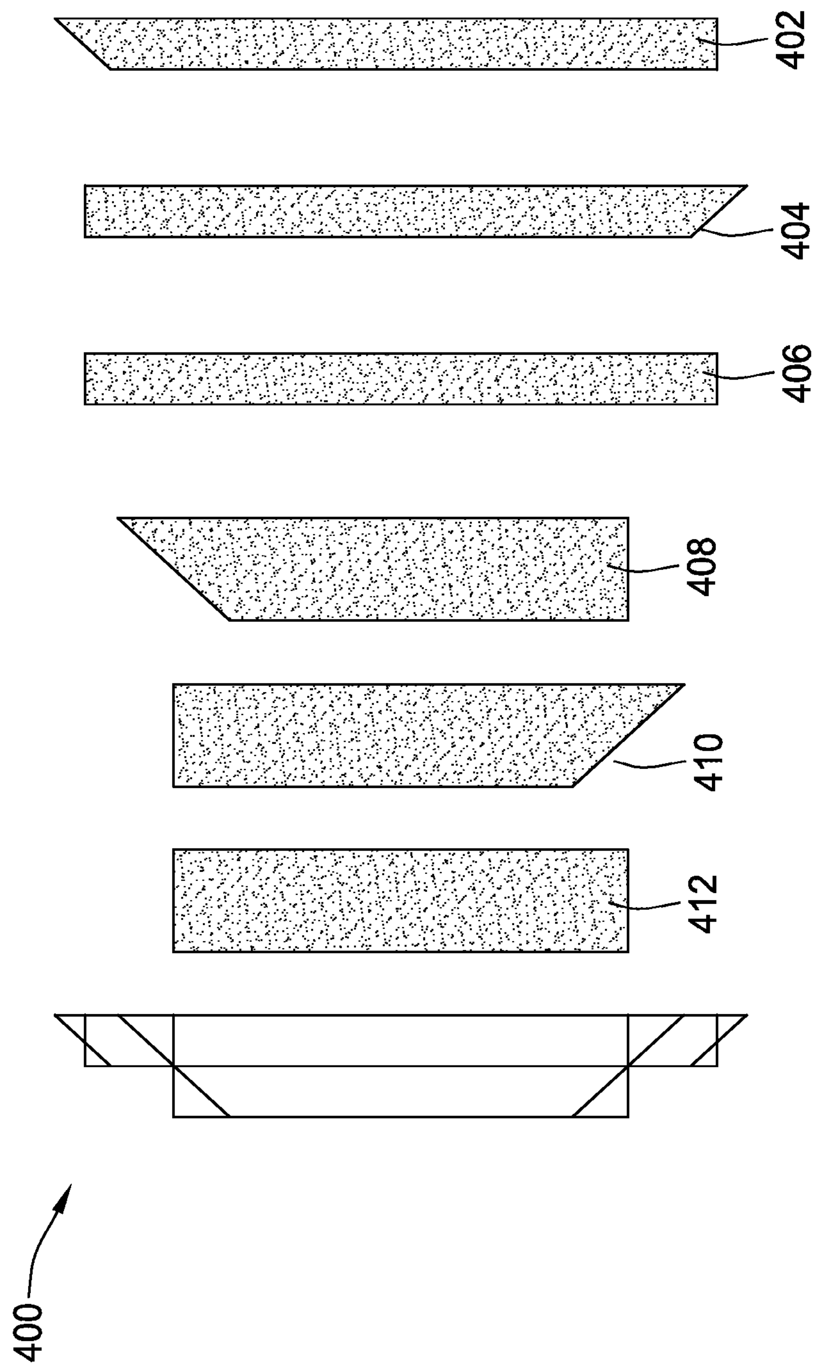
FIG. 4B shows cross-sections of different fastening features that may be used for different drugs, drawn on a longitudinal plane.

The cross-sectional shape of the coding features may vary in any plane, e.g. transverse, longitudinal, radial, or normal to helix. Likewise the shape of the stop feature can be varied. FIG. 4A shows cross-sectional slices through the transverse plane of several examples of different coding features, 402, 404, 406, and 408. To illustrate the diversity of these shapes the cross-sectional slices are overlaid as 400. Each of these coding features might be used for a different medicament. The cross-section for each drug is larger in one area and smaller in another than for all of the other drugs, which can be seen by overlaying all of the cross-sections in sketch 400. In this way, if the wrong cartridge holder in the collection is inserted into the wrong dose setting member, the parts cannot be fully assembled. FIG. 4B shows the same coding features as cross-sections, but through the longitudinal plane (i.e. the plane normalized to the curvature of the coding features. The shapes of the coding features can be more complex than that shown in the figures and can include various indentations or protrusions along any of the edges.

Each coding feature may vary in shape and size. For instance, as shown in FIG. 4A each coding feature may vary in radial extent and/or circumferential extent (e.g., pins 402-406 are both radially narrower and circumferentially longer than pins 408-412). While not shown, pins may also vary in axial extent. Further, the edges of the pins may vary angularly. For example, as shown, both edges of pin 402 and both edges of pin 408 are normal to the circumference of the coding feature (and thus to the circumference of the outer cylindrical wall of the cartridge holder), while pins 404, 406, 410, and 412 each include one edge that is normal to the circumference, and one edge that is angled relative to the circumference.

Figure 4C:
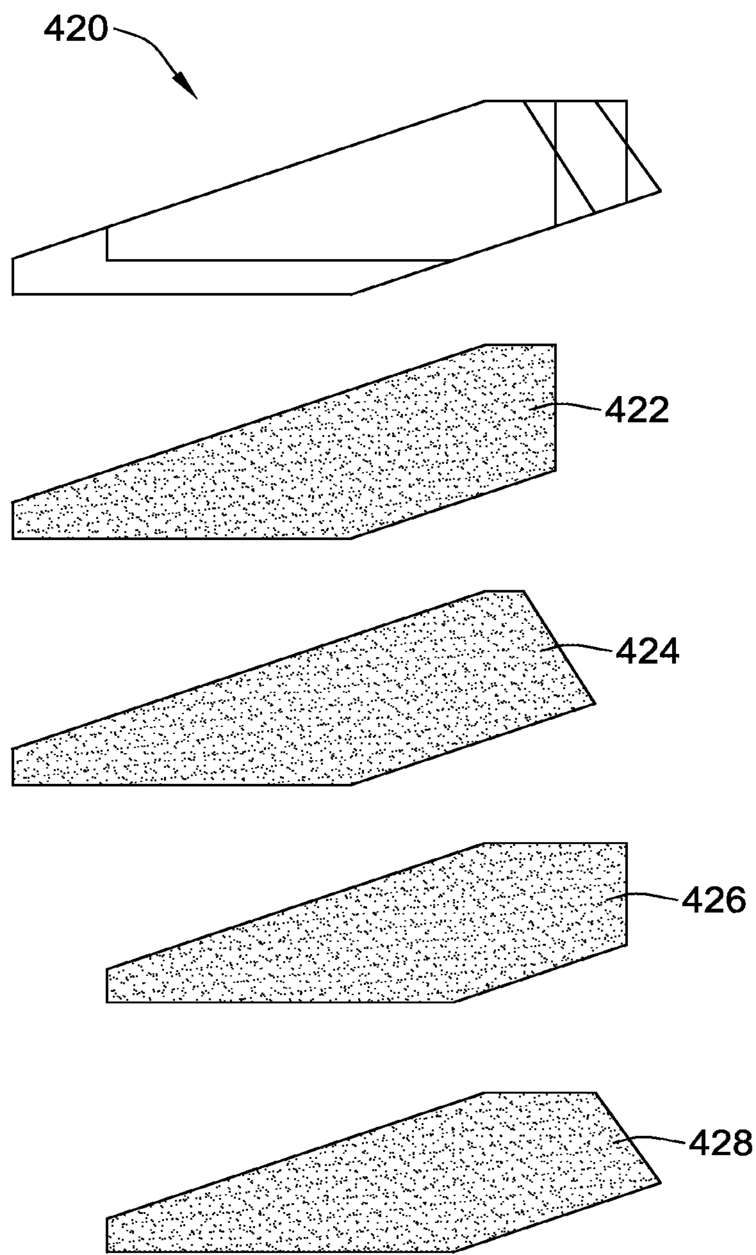
FIG. 4C shows shapes of different fastening features that may be used for different drugs, drawn as a projection around the circumference.

The pin feature on the dose setting member may also vary in size and/or shape. For example, FIG. 4C shows various possible shapes of coding features located on the dose setting member projected around the circumference. Superimposing the different pins 420 illustrates the shape differences of each possible pin. Additionally, the pins 422-428 may include a differing number of axial, rotational, and/or helical surfaces. The length of the axial surface(s), rotational surface(s), and/or helical surface(s) on each of pins 422-428 may also differ. Further, the edges of pins 422-428 may vary in angle relative to the longitudinal plane (not shown), and may vary in other aspects as well. Each of these variations in pin shapes 422-428 may be used so that a cartridge holder may be coded to the particular structure of the pin feature 420, such as by incorporating coding features that are coded to match the pins 422-428 on the dose setting member. Accordingly, a particular series of movements in the axial, helical, and/or rotational may be required to connect the cartridge holder to a dose setting member.

Figure 5:
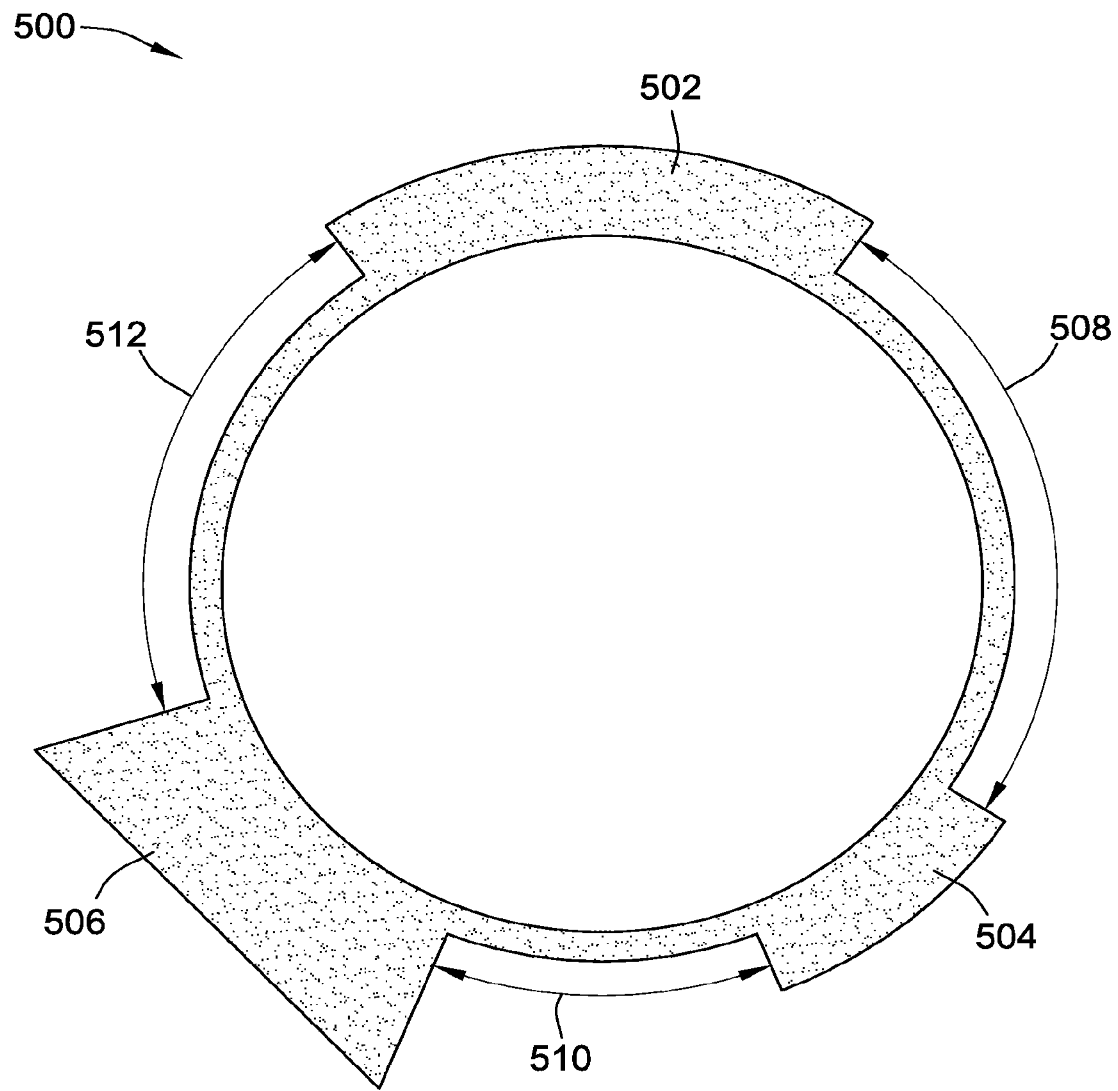
FIG. 5 shows a cross-section in a transverse plane of a dose setting member having multiple pin features.

In one embodiment, the cartridge holder may include multiple ridge features that are coded to match multiple pin features in a dose setting member. FIG. 5 shows a cross-section of a dose setting member 500 having multiple pin features 502-506, through the transverse plane. Preferably, pin features 502-506 are shaped and/or arranged asymmetrically such that the spacing between the pin features 502-506 is also asymmetrical. As a result, a cartridge holder may be coded with ridge features that, when initially inserted into the corresponding dose setting member (or one of a group of corresponding dose setting members), substantially fill the gaps 508-512 (i.e. are of substantially the same size and shape). By coding the cartridge holder with such ridge features, a user may be required to align the cartridge holder and dose setting member 500 in a specific position relative to each other in order to connect the cartridge holder to the dose setting member 500, which increases the number of coding combinations relative to a system where the pins are symmetrically arranged around the circumference.

Figure 6:
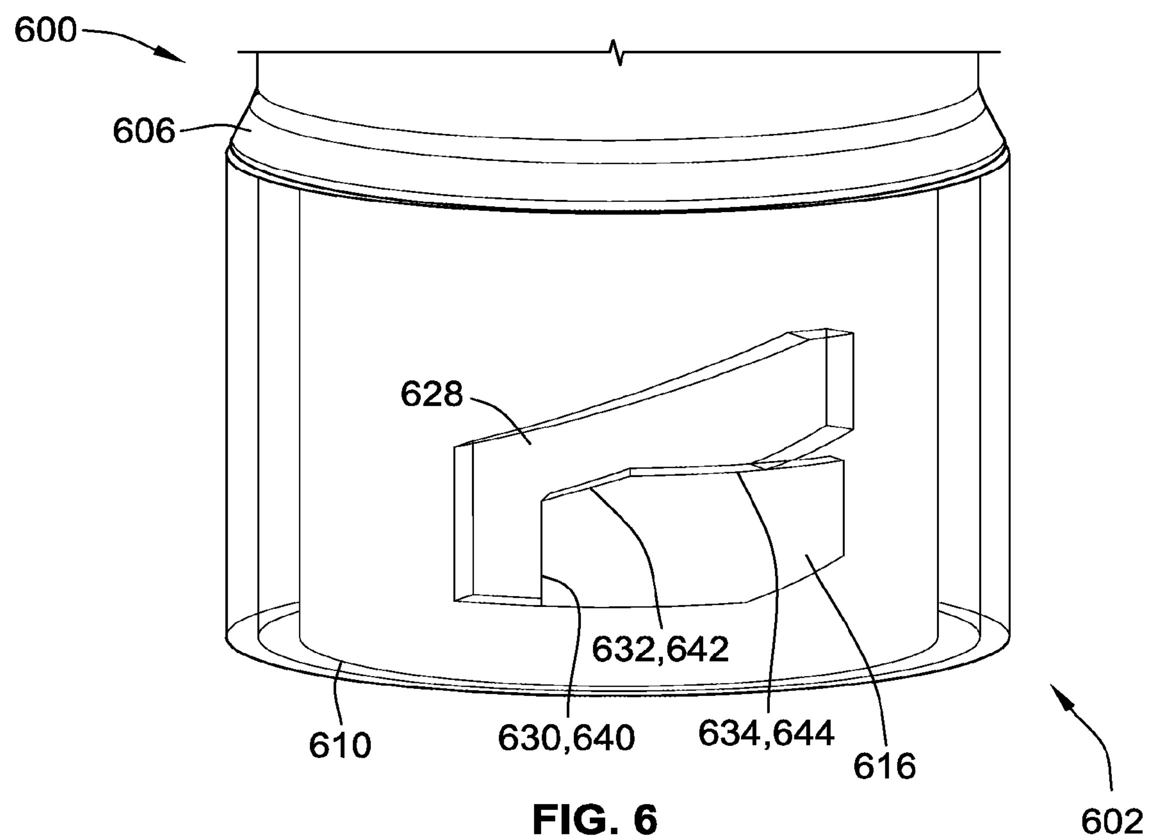
FIG. 6 illustrates another arrangement of a cartridge assembly that includes coding features to help dedicate the cartridge assembly to a particular dose setting member.

FIG. 6 illustrates an embodiment of a cartridge holder 600 that includes fastener and coding features to help dedicate the cartridge holder 600 to a particular dose setting member 602.

The cartridge holder 600 has a shoulder 606 and a proximal end. Cartridge holder 600 is generally similar in structure to cartridge holder 300, except that cartridge holder 600 employs a pin feature 616, which is coded to match a pin feature 628 on dose setting member 602, rather than a ridge feature. Pin feature 616 protrudes radially outward from the cylindrical outer wall of the connector portion of cartridge holder 600. As shown, the pin feature 616 is coded to match the pin feature 628 of dose setting member 602. In this embodiment, the radial extent of the pin feature 628 is substantially equal to the radial extent of the pin feature 616. When connected, axial surface 630, helical surface 632, and rotational surface 634 of the first pin sit flush against axial surface 640, helical surface 642, and rotational surface 644 of pin feature 628 respectively, helping secure the cartridge holder 600 to the dose setting member 602.

Figure 7:
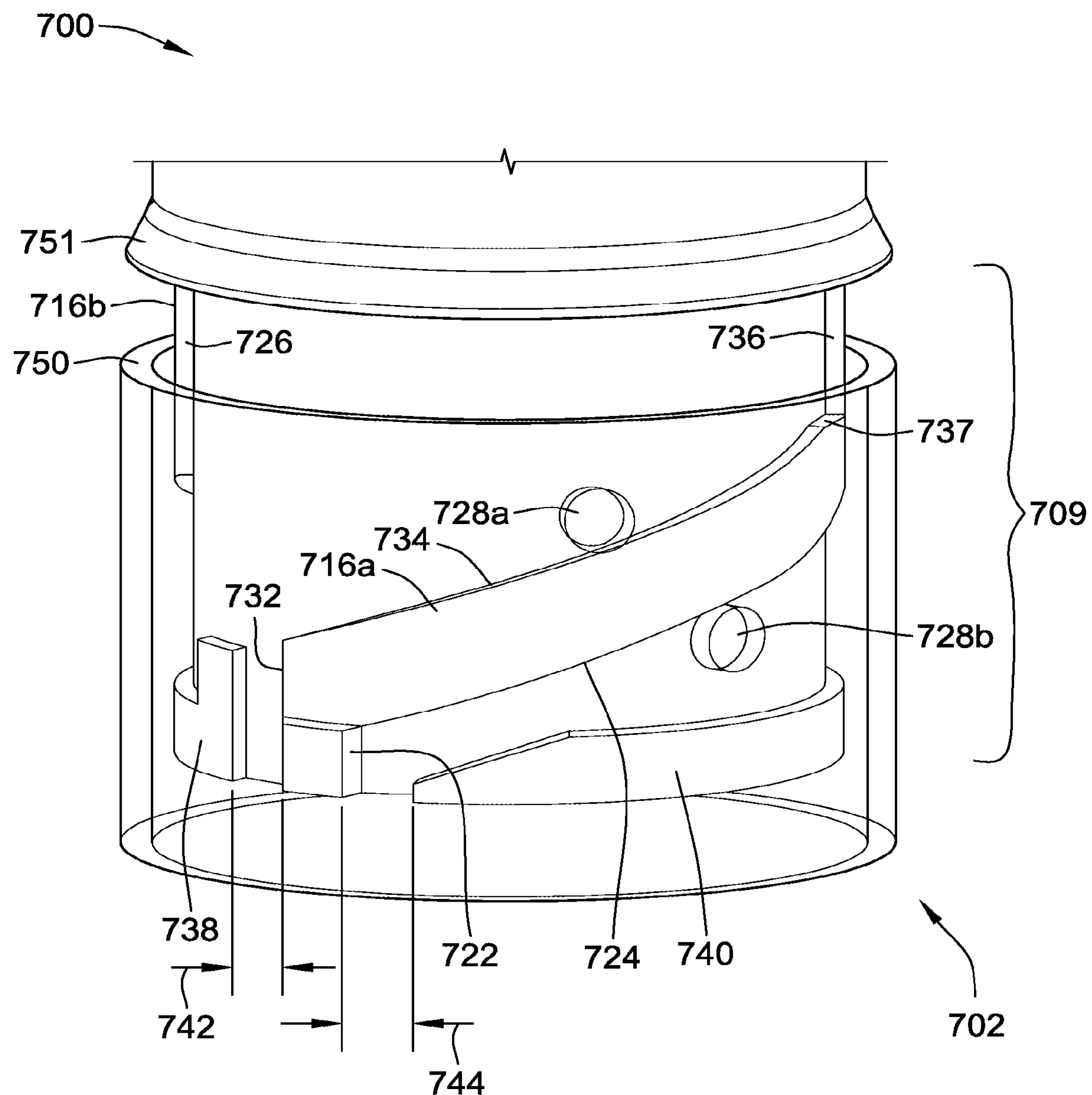
FIG. 7 illustrates an arrangement of a cartridge assembly that includes coding features to help dedicate the cartridge assembly to a dose setting member having pin features and that are axially offset from each other.

FIG. 7 illustrates an embodiment in which a cartridge holder 700 that includes coding features to help dedicate the cartridge holder 700 to a dose setting member 702 having pin features 728*a* and 728*b* that are axially offset from each other (more specifically, pin features 728*a* and 728*b* are helically offset; i.e. offset both axially and rotationally from each other). Cartridge holder 700 includes ridge features 716*a* and 716*b*. Ridge features 716*a* and 716*b* are symmetric across the diameter of the cartridge holder, and thus, the embodiment may be described with reference to ridge feature 716*a*. It should be understood that description of ridge feature 716*a* applies equally to ridge feature 716*b* and vice versa.

Ridge feature 716*a* includes a distal edge and a proximal edge. As shown, the proximal edge includes a first axial surface 722 that is generally parallel to, but of a shorter axial extent than, a first axial surface 732 of the distal edge. The proximal edge also includes a helical surface 724 that is generally parallel to a helical surface 734 of the distal edge. The distal edge then includes a rotational surface 737, but a rotational surface is not essential on the proximal edge. Further, the proximal edge includes a second axial surface 726 that is generally parallel to, but of a longer axial extent than, a second axial surface 736 of the distal edge.

Ridge feature 716*a* is coded to match the pair of pin features 728*a* and 728*b* on dose setting member 702. The pair of pin features on the dose setting member 702 includes a distal pin feature 728*a* and a proximal pin feature 728*b*, which are helically offset from each other. Cartridge holder 700 also includes coding features 738 and 740, which are located along the proximal end of connecting portion 709. Coding feature 738 is arranged to form a gate 742 between the axial surface 732 of the distal edge and the coding feature 738, and coding feature 740 is arranged to form a gate 744 between the axial surface 722 of the proximal edge and the coding feature 740. Each gate 742, 744 has a circumferential extent at least equivalent to the circumferential extent of pin features 728*a* and 728*b*.

With the illustrated embodiment, the cartridge holder 700 may thus be connected to the dose setting member 702 by performing the following: (1) positioning the cartridge holder so that gates 742 and 744 are aligned with pin features 728*a* and 728*b*, and then moving the cartridge holder 700 in the axial direction, such that pin feature 728*a* is guided axially along the first axial surface 732 of the distal edge of ridge feature 716*a*, and pin feature 728*b* is guided axially along the first axial surface 722 of the proximal edge, and (2) moving the cartridge holder 700 in the helical direction, such that pin feature 728*a* is guided helically along the helical surface 734 of the distal edge, and pin feature 728*b* is guided helically along the helical surface 724 of the proximal edge. When the distal end 750 of the device contacts the proximal shoulder 751 of the cartridge holder, the cartridge holder is rotated until pin feature 728*a* contacts the second axial surface 736 of the distal edge, thereby preventing further movement and securing the cartridge holder 700 to the dose setting member 702.

Gates 742 and 744 are arranged such that these gates accept the pin features 728*a* and 728*b*, respectively, in order to connect cartridge holder 700 to dose setting member 702. As such, the ridge feature 716*a* and coding features 738 and 740 may be arranged to create gates that will accept dose setting members intended for use with the medicament in the cartridge holder. For example, in the illustrated embodiment, pin features 728*a* and 728*b* are the same size, and thus, gates 742 and 744 are also the same size. In other embodiments, however, pin features 728*a* and 728*b* may differ in size, and accordingly, coding features 742 and 744 may be arranged such to form gates that also differ in size to match the pin features. Additionally, the cross-sectional size and/or shape of ridge 734 can be varied. In the embodiment of FIG. 7, if the user inadvertently aligns pin 728*a* with gate 744, it will not be possible to assemble the cartridge holder. To prevent this error, pin 728*a* could be made larger than gate 744, for example with a larger circumferential extent.

Figure 8:
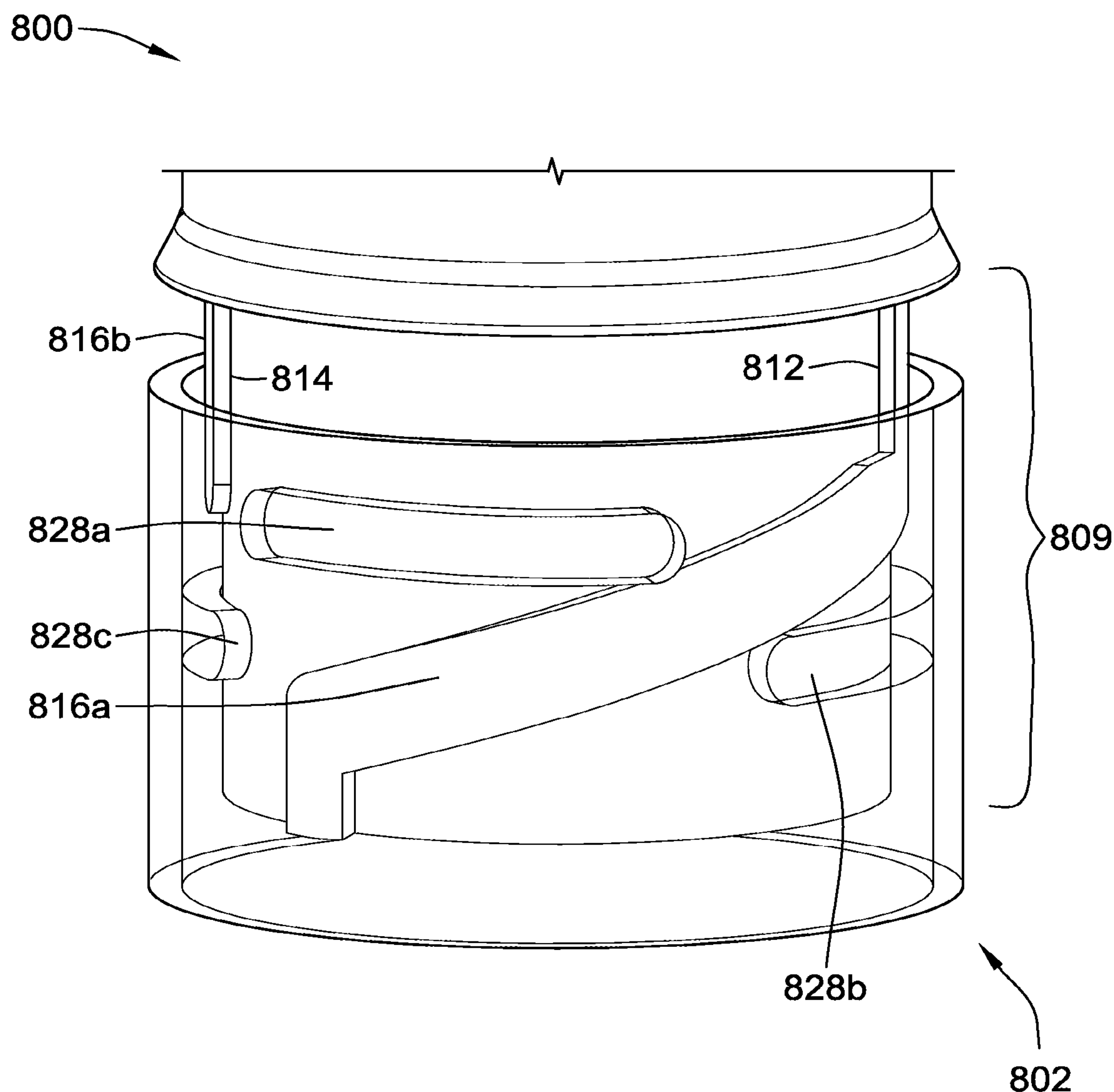
FIG. 8 illustrates an arrangement of a cartridge holder that includes two ridge features to help dedicate the cartridge assembly to a dose setting member having pin features and that are axially offset from each other.

FIG. 8 illustrates an alternative method to prevent assembly errors, using a cartridge holder 800 having two ridge features 816*a* and 816*b*. On the outer cylindrical wall of connector portion 809, ridge feature 816*a* is directly opposite ridge feature 816*b* (i.e., ridge features 816*a* and 816*b* are symmetrical across the diameter of connector portion 809). As such, the circumferential extent $CE_1$ between the distal edge 812 of ridge feature 816*a* and the proximal edge 814 of ridge feature 816*b* is equal to the circumferential extent between the proximal edge of ridge feature 816*a* and the distal edge of ridge feature 816*b*.

This arrangement of ridge features 816*a* and 816*b* is coded to match oblong pin features 828*a*, 828*b*, and 828*c* on a dose setting member 802. The length of the pins is such that there is insufficient space for the ridge feature to fit between pins 828*a* and 828*c*; pins 828*a* and 828*c* may also be joined together to prevent incorrect assembly. The circumferential extent between pins 828*a* and 828*b* is similar to the circumferential extent of the proximal end of the ridge feature 816*a*. Thus, when cartridge holder 800 is initially inserted into dose setting member 802, and pin features 828*a* and 828*b* have engaged the ridge feature 816*a*, rotational movement of the cartridge holder 800 is substantially blocked, as the ridge feature 816*a* fits securely between pin features 828*a* and 828*b*. On the other hand, if a user attempts to insert cartridge holder 800 (shown in FIG. 8) into a dose setting member intended for a different cartridge holder the coding may either prevent assembly, or cause the assembly to be too loose to function correctly. This may indicate to the user that they are not using the correct dose setting member or cartridge holder.

Figure 9A:
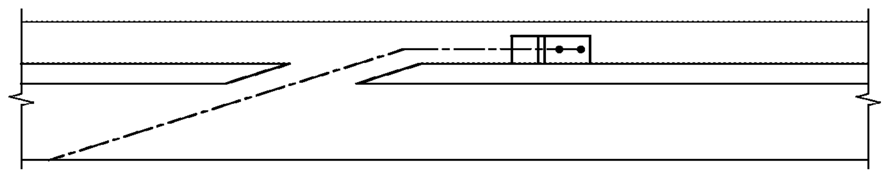
FIG. 9 illustrates a detent that can be used to help dedicate the cartridge assembly to a dose setting mechanism.
Figure 9A:
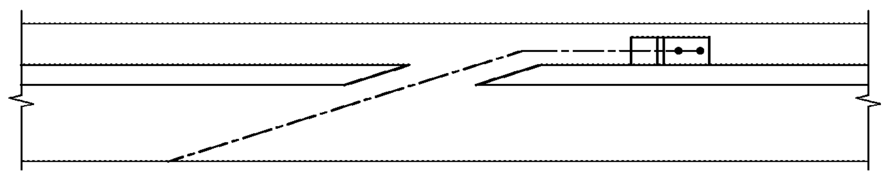
Figure 9A:
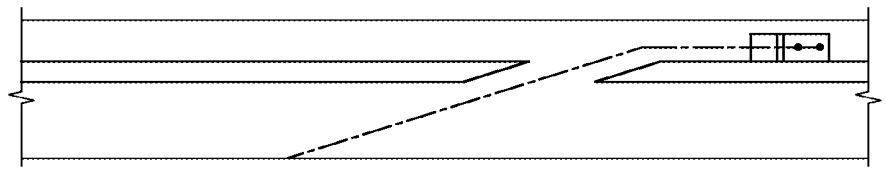
Figure 9B:
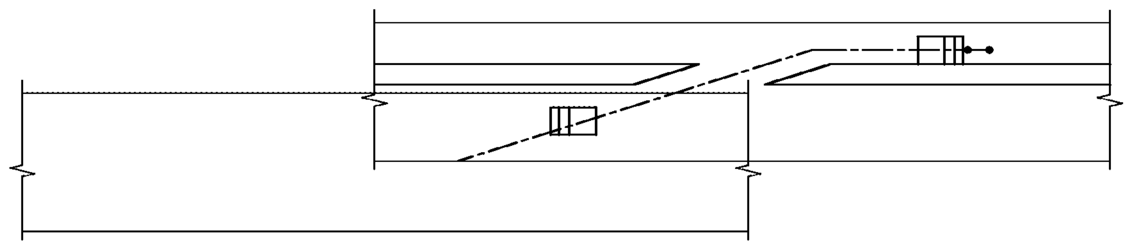
Figure 9C:
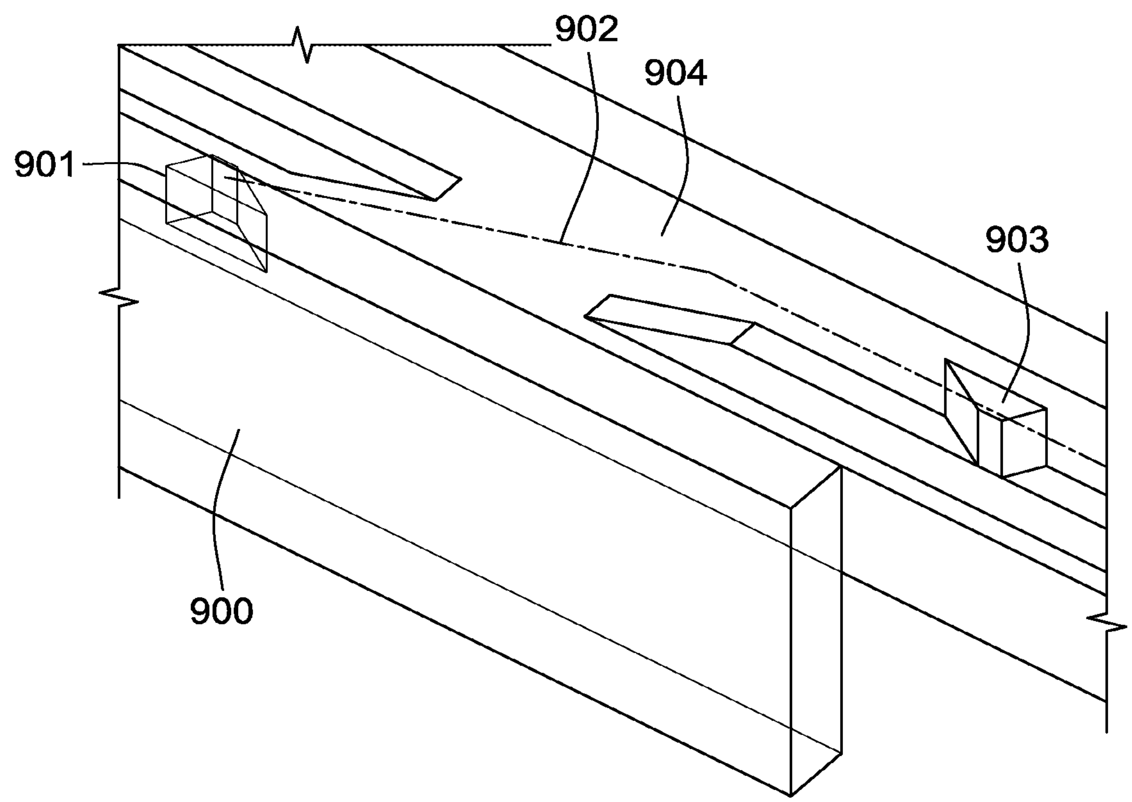

In a further aspect, coding of a cartridge holder to a dose setting member may be accomplished by arranging a ridge feature or pin feature (on either the cartridge holder or dose setting member) such that the ridge or pin feature locks in a corresponding detent when the cartridge holder and dose setting member are properly connected. FIG. 9 shows one example of such a locking coding feature where the dose setting member 900 has a protruding detent 901 that follows a path 902 along cartridge assembly 904 during connection. FIG. 9A shows fastener coding features for use on three different cartridge assemblies in a collection each containing three different medicaments. FIG. 9B shows the path of a protrusion on the cartridge holder during fastening. Detent 901 eventually snaps over detent 903 on the cartridge assembly locking the two pieces together. Thus, if a cartridge holder is connected to an incompatible dose setting member, either it would not lock into place (i.e., it would be loose), or its travel would be blocked prior to fully connecting (e.g., prior to the distal end of the dose setting member contacting the shoulder of the cartridge holder). Further, a spring could be incorporated in a dose setting member to push a cartridge holder out of the dose setting member when not properly connected.

Figure 10A:
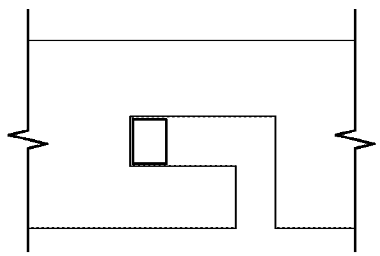
FIGS. 10A and 10B illustrated how coding may depend on the size or position in more than one dimension, specifically the size or position of a coding feature in more than one dimension.
Figure 10B:
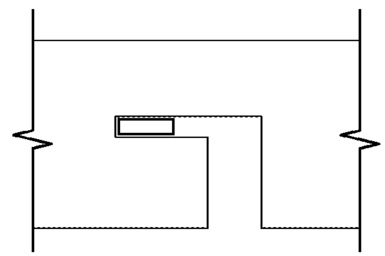
Figure 11A:
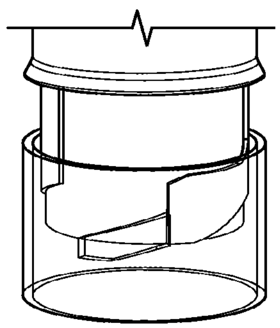
FIGS. 11A and 11B illustrate another embodiment of how coding may depend on the size or position in more than one dimension, specifically where
Figure 11B:
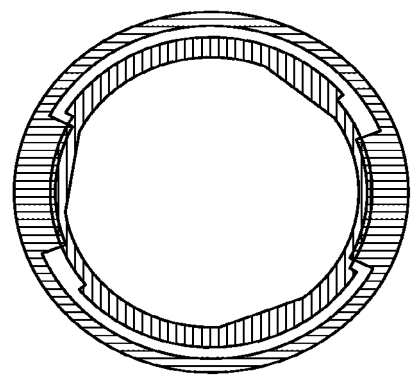

In a further aspect, the cartridge assembly may fit, in particular to the dose setting member, in one or more orientations. If the cartridge assembly fits in only one orientation, the number of coding combinations may be increased. This might be achieved if one or more coding features integral to the fastener (e.g., pins) have an asymmetric position or size around the axis, or if one of the features is unique, e.g., an indentation that is smaller than all the others. Coding may depend on the size or position in more than one dimension. This is illustrated in FIGS. 10 and 11, where FIGS. 10A and 10B show a variation of the size or position of a coding feature in more than one dimension. FIG. 11A shows a pin coded by its circumferential extent and axial position and FIG. 11B shows a pin with a small circumferential extent and a large radial extent, incorrectly mated to a groove that is intended to mate to a pin with a large circumferential extent and a small radial extent. A coding system for a collection of different medicaments may consist of a different fastening feature for each medicament, each of which is smaller in one dimension and larger in another than all of the other features in the system. For example, a pin with a small circumferential extent will fit into the space for a wider pin, but if it has a larger axial extent it will not rotate. Alternatively, a pin with a small circumferential extent may have a large radial extent, and therefore the cartridge assembly cannot be inserted into the wrong device. Each feature may be offset in an axial direction relative to the others, increasing the number of coding combinations, and in addition, the fastening features may have an asymmetric position or size relative to each other when viewed along a longitudinal axis. In some embodiments of this disclosure all pins are on the dose setting member, the pins could equally be on the cartridge assembly or alternatively, one or more pins could be on the cartridge assembly, and the rest on the dose setting member.

Figure 14:
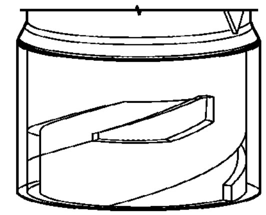
FIG. 14 illustrates an arrangement where the coding features integral to the fastener of the cartridge holder are located on the outer cylindrical surface of the tubular member and are of the pin and groove type of fastener.

Alternatively or additionally, the cartridge assembly could be fastened to the dose setting member by a pin that is guided along a groove, where the pin could be located on the cartridge holder and the groove on the dose setting member or vice versa. Such a fastener assembly is depicted in FIG. 14 where the pin and groove are configured to match and therefore prevent attaching the wrong cartridge assembly to the wrong dose setting member.

Figure 12:
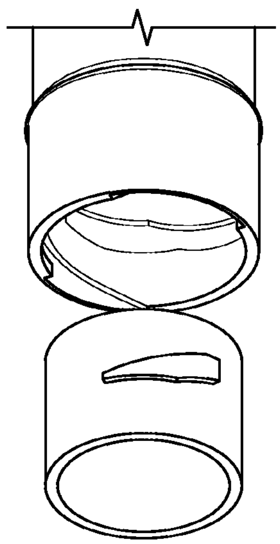
FIG. 12 illustrates an arrangement where the coding features integral to the fastener of the cartridge holder are located on the inner cylindrical surface of the tubular member.

FIG. 12 illustrates an arrangement where the coding features integral to the fastener of the cartridge holder are located on the inner cylindrical surface of the tubular member.

Figure 13:
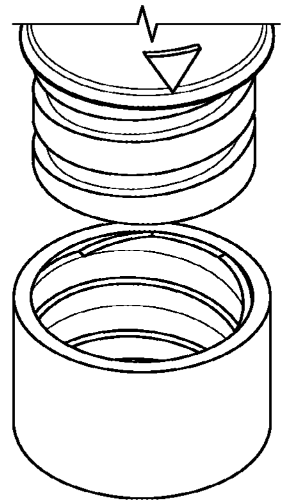
FIG. 13 illustrates an arrangement where the coding features integral to the fastener of the cartridge holder are located on the outer cylindrical surface of the tubular member and are of the screw thread type of fastener.

Yet another alternative or additional way is where the coding feature integral to the fastener is a screw thread and a different thread type could be used for (or matched to) each different medicament in a collection of cartridge assemblies. One such example is illustrated in FIG. 13. In the case of a thread, the coding feature could be the crest of the thread with each having a different circumferential extent to the trough, or turns in the thread would be unequally spaced around the circumference. In another example, a thread with a small circumferential extent will fit into the space for a wider thread, but if it has a larger axial extent it will not rotate. Alternatively, a thread with a small circumferential extent may have a large radial extent, and therefore the cartridge assembly cannot be inserted into the device.

In another aspect of the disclosure, coding features (e.g., ridge and pin features) may be detected by electronic verification features; e.g. electrical or optical sensors, microswitches, optical switches, magnetic switches, etc. For example, when a cartridge holder is connected to the correct dose setting member, a switch on an edge of a coding feature (on the cartridge holder and/or the dose setting member) may be triggered. As another example, a sensor on the dose setting member may be configured to detect the coding feature of cartridge holder. The sensor may be located so that it only aligns with (and thus detects) the coding feature on the cartridge holder when properly connected. As such, a programmable drug delivery device may be disabled until the switch is triggered or sensors are brought into alignment, helping prevent incorrect administration of medicament.

The cartridge holders and dose setting members described herein help provide a large number of different coding configurations. Consequently, with proposed coding features, a large number of medicaments can be distinguished from one another. In addition, with the proposed coding features, if a user attempts to load an incorrect reservoir into a cartridge holder designed for a different cartridge, the user will be alerted at an early stage of the assembly process. Particularly, in a collection of cartridge assemblies and dose setting members which are provided to form drug delivery devices, each comprising a separate cartridge assembly and a separate dose setting member, it may, as provided by this disclosure, be prevented that cartridge assemblies are assembled together with a wrong dose setting member to form a delivery device which delivers an incorrect amount of medicament or a medicament other than the correct amount or medicament for which it was designed.

Exemplary embodiments of the present disclosure have been described. It should be understood that, in general, the functionality and structural aspects described herein with reference to ridge features on a cartridge holder may apply equally with respect to ridge features on a dose setting member, and vice versa with respect to pin features on a cartridge holder. Those skilled in the art will understand, however, that changes and modifications may be made to these arrangements without departing from the true scope and spirit of the present disclosure, which is define by the claims.

We claim:

1. A collection comprising a plurality of cartridge assemblies each having one or more coded fasteners for connecting different medicaments to specifically matched dose setting members of the collection to make up a family of delivery devices, the collection comprising:

two or more cartridge assemblies, where a first cartridge assembly comprises, a) a first medicament; and b) a fastener comprising a first coding feature that is unique to the first medicament and is specifically coded to engage a complementary coding feature on a fastener on a first dose setting member that is configured to dispense the first medicament, wherein the first coding feature is different than a second coding feature on a fastener on a second cartridge assembly in the collection that contains a second medicament, where the first and second medicaments are different and where the second cartridge assembly will not operably connect to the first dose setting member, thereby preventing the first dose setting member from administering the second medicament, wherein each fastener in the collection of cartridge assemblies is coded by a position of the fastener relative to a detent, where the detent is configured as a protrusion that snaps over a corresponding detent of the fasteners on the dose setting members into a locking position when rotated relative to the fasteners on the dose setting members to operably connect a cartridge assembly to a dose setting member.

2. The collection of claim 1, further comprising a third cartridge assembly having a fastener comprising a third coding feature unique to a third medicament contained in the third cartridge assembly that is different than the first and second medicaments and where the third cartridge assembly operably connects to a third dose setting member that is different from other dose setting members in the family of delivery devices.

3. The collection of claim 1, wherein all the fasteners of the cartridge assemblies in the collection are of the same type selected from the group consisting of threads, pins & grooves, pins & ridges, bayonet, snap-fit, and detents, and wherein each coding feature on each fastener is different from all the other coding features on the other fasteners on the cartridge assemblies in the collection.

4. The collection of claim 1, wherein each fastener on each of the cartridge assemblies in the collection is of a different type and is selected from the group consisting of threads, pins & grooves, pins & ridges, bayonet, snap-fit, and detents, and wherein each coding feature on each fastener is different from all the other coding features on the other fasteners on the cartridge assemblies in the collection.

5. The collection of claim 1, where each fastener in the collection of cartridge assemblies has two or more coding features.

6. The collection of claim 1, where each coding feature of each fastener in the collection of cartridge assemblies comprises at least one protrusion that has a ridge feature and where all the complementary coding features on all of the dose setting members in the collection comprise a pin feature configured to engage the ridge feature.

7. The collection of claim 1, where each coding feature of each fastener in the collection of cartridge assemblies comprises at least one groove configured to accept a pin located on all the complementary coding features on all of the dose setting members in the collection.

8. The collection of claim 1, where each coding feature of each fastener in the collection of cartridge assemblies comprises a pair of pins, and the complementary coding feature on the dose setting member comprises a ridge feature, wherein the pins are axially offset from each other.

9. The collection of claim 1, where each fastener in the collection of cartridge assemblies comprises a screw thread and each coding feature of each fastener has a different pitch, number of turns, or angle of threads that is unique to a specific medicament.

10. The collection of claim 1, where each coding feature of each fastener in the collection of cartridge assemblies comprises at least one pin and where all the complementary coding features on all of the dose setting members in the collection comprise a complementary pin feature.

11. The collection of claim 1, where the first cartridge assembly comprises a tubular member, the first medicament being provided in the tubular member.

12. The collection of claim 11, where the fastener of the first cartridge assembly is provided at a proximal end of the tubular member.

13. The collection of claim 12, where the tubular member has a cylindrical inner surface and a cylindrical outer surface, the fastener being provided on the cylindrical inner surface or on the cylindrical outer surface.

14. The collection of claim 1, where the respective delivery device is an injection device.

15. A family comprising a plurality of delivery devices, each delivery device comprising a cartridge assembly containing a medicament, the cartridge assembly being connected to an associated dose setting member to form the delivery device, the dose setting members and cartridge assemblies of the plurality of delivery devices being chosen from a collection as claimed in any of the previous claims, wherein the cartridge assemblies and dose setting members are configured such that the cartridge assembly of one of the delivery devices will not connect to the dose setting member of another one of the plurality of delivery devices and such that the dose setting member of one of the delivery devices will not connect to the cartridge assembly of another one of the delivery devices.

* * * * *